United States Patent
Stanford et al.

(10) Patent No.: US 7,008,524 B2
(45) Date of Patent: *Mar. 7, 2006

(54) SENSORS WITH VARIABLE RESPONSE BEHAVIOR

(75) Inventors: Thomas B. Stanford, Port Hueneme, CA (US); Camille I. Van Ast, Newbury Park, CA (US); Frederick G. Yamagishi, Newbury Park, CA (US)

(73) Assignee: HRL Laboratories, LLC, Malibu, CA (US)

( * ) Notice: Subject to any disclaimer, the term of this patent is extended or adjusted under 35 U.S.C. 154(b) by 344 days.

This patent is subject to a terminal disclaimer.

(21) Appl. No.: 10/230,947

(22) Filed: Aug. 29, 2002

(65) Prior Publication Data

US 2003/0062263 A1 Apr. 3, 2003

Related U.S. Application Data

(63) Continuation-in-part of application No. 09/679,428, filed on Oct. 3, 2000, now Pat. No. 6,730,212, and a continuation-in-part of application No. PCT/US01/28717, filed on Sep. 10, 2001.

(60) Provisional application No. 60/316,111, filed on Aug. 29, 2001.

(51) Int. Cl.
*G01N 27/327* (2006.01)
*C12Q 1/00* (2006.01)

(52) U.S. Cl. .............. 205/777.5; 205/792; 204/403.01; 435/4

(58) Field of Classification Search ............ 422/82.02, 422/83, 98; 204/403.01; 205/777.5, 792; 435/4, 5, 7.1, 7.9, 14, 25, 26, 28
See application file for complete search history.

(56) References Cited

U.S. PATENT DOCUMENTS

| | | | |
|---|---|---|---|
| 4,019,367 A | 4/1977 | Norsworthy | |
| 4,334,880 A | 6/1982 | Malmros | |
| 4,444,892 A | 4/1984 | Malmros | |
| 4,457,161 A | 7/1984 | Iwanaga et al. | |
| 4,624,756 A | 11/1986 | Matsuda et al. | |
| 4,674,320 A | 6/1987 | Hirschfeld | |

(Continued)

FOREIGN PATENT DOCUMENTS

EP 0 596 973 B1 12/1995

(Continued)

OTHER PUBLICATIONS

Melloni's Pocket Medical Dictionary Illustrated, 2004, p. 350.*

(Continued)

*Primary Examiner*—Kaj K. Olsen
(74) *Attorney, Agent, or Firm*—Ladas & Parry LLP

(57) ABSTRACT

A sensor and method for detecting biological and chemical agents comprising metal interdigitized electrodes coated with hybrid polymer-based conducting film and an instrument for applying electrical voltage to the electrodes and registering the change in electrical current. The hybrid film also comprises indicator biomolecules encapsulated within the film or attached to it. The bioindicator molecules preferably comprise enzyme acetylcholinesterase. When these indicator biomolecules come in a contact with a pathogen, chemical and/or morphological changes occur in the film and electrical current flowing through the electrodes is modulated. The pathogen comprise inhibitors of enzymes, preferably organophosphates, thiophosphates or phosphonates. The change in current indicates the presence of a biological and chemical agent and is registered.

67 Claims, 6 Drawing Sheets

U.S. PATENT DOCUMENTS

| | | | |
|---|---|---|---|
| 4,699,804 A | 10/1987 | Miyata et al. | |
| 4,721,601 A | 1/1988 | Wrighton et al. | |
| 4,822,465 A | 4/1989 | Jones et al. | |
| 4,907,441 A | 3/1990 | Shurmer | |
| 4,977,658 A | 12/1990 | Awano et al. | |
| 5,018,380 A | 5/1991 | Zupancic et al. | |
| 5,086,286 A | 2/1992 | Yasukawa et al. | |
| 5,122,237 A | 6/1992 | Kim et al. | |
| 5,208,301 A | 5/1993 | Epstein et al. | |
| 5,234,566 A | 8/1993 | Osman et al. | |
| 5,312,762 A | 5/1994 | Guiseppi-Elie | |
| 5,331,287 A | 7/1994 | Yamagishi et al. | |
| 5,337,018 A | 8/1994 | Yamagishi | |
| 5,372,785 A | 12/1994 | Johnson et al. | |
| 5,407,699 A | 4/1995 | Myers | |
| 5,417,100 A | 5/1995 | Miller et al. | |
| 5,491,097 A | 2/1996 | Ribi et al. | |
| 5,520,852 A | 5/1996 | Ikkala et al. | |
| 5,536,473 A | 7/1996 | Monkman et al. | |
| 5,540,862 A | 7/1996 | Cao et al. | |
| 5,571,401 A | 11/1996 | Lewis et al. | |
| 5,607,573 A | 3/1997 | Miller et al. | |
| 5,622,872 A * | 4/1997 | Ribi ............................ | 436/518 |
| 5,624,605 A | 4/1997 | Cao et al. | |
| 5,625,139 A | 4/1997 | Stormbom | |
| 5,698,083 A | 12/1997 | Glass | |
| 5,756,879 A | 5/1998 | Yamagishi et al. | |
| 5,766,934 A | 6/1998 | Guiseppi-Elie | |
| 5,922,537 A | 7/1999 | Ewart et al. | |
| 5,928,609 A | 7/1999 | Gibson et al. | |
| 6,730,212 B1 | 5/2004 | Yamagishi et al. ...... | 205/777.5 |
| 2004/0092004 A1 | 5/2004 | Stanford, Jr. et al. .... | 435/287.1 |

FOREIGN PATENT DOCUMENTS

| | | |
|---|---|---|
| GB | 2 225 008 | 5/1990 |
| GB | 2 237 291 | 5/1991 |
| JP | 58-176538 | 10/1983 |
| JP | 63-215960 | 9/1988 |
| JP | 03-089156 | 4/1991 |
| JP | 05-296960 | 11/1993 |
| WO | 88/09808 | 12/1988 |
| WO | 95/32422 | 11/1995 |
| WO | 97/04464 | 2/1997 |
| WO | 98/19153 | 5/1998 |
| WO | 02/29378 | 4/2002 |

OTHER PUBLICATIONS

Akkara, J., et al., "Synthesis of Two-Dimensional Electrooptic Polymer Networks Through Biocatalysis," *Polymer Preprints*, vol. 34, No. 2, pp 759-760 (Aug. 1993).

Araujo, Y.C., et al., "Structure of Silane Films and Their Adhesion Properties," *Mat. Res. Soc. Symp. Proc.*, vol. 407, pp 325-330 (1996).

Arkles, B., "Silane Coupling Agent Chemistry," *Silicon Compounds: Register and Review*, 5th Ed., pp 59-64 (1991).

Bartlett, P., et al., "Conducting Polymer Gas Sensors, Part I: Fabrication and Characterization," *Sensors and Actuators*, vol. 19, pp 125-140 (1989).

Bartlett, P., et al., "Conducting Polymer Gas Sensors, Part III: Results for Four Different Polymers and Five Different Vapours," *Sensors and Actuators*, vol. 20, pp 287-292 (1989).

Brumlik, C.J., et al., "Template Synthesis of Metal Microtubules," *J. Am. Chem. Soc.*, vol. 113, pp 3174-3175 (1991).

Buehler, M.G., et al., "Gas Sensor Test Chip," *Proceedings of the 1996 IEEE International Conference on Microelectronic Test Structures*, vol. 9, pp 105-110 (Mar. 1996).

Charlesworth, J.M., et al., "Mechanistic Studies on the Interactions Between Poly(pyrrole) and Organic Vapors," *J. Phys. Chem.*, vol. 97, pp 5418-5423 (1993).

Cui, C.X., et al., "Two helical conformations of polythiophene, polypyrrole, and their derivatives," *The American Physical Society, Physical Review B*, vol. 40, No. 14, pp 9661-9670 (Nov. 15, 1989).

Cullen, D.C., et al., "Multi-analyte miniature conductance biosensor," *Analytica Chimica Acta*, vol. 231, pp 33-40 (1990).

Dave, B.C., et al., "Sol-gel Encapsulation Methods for Biosensors," *Analytical Chemistry*, vol. 66, No. 22, pp 1120A-1127A (Nov. 15, 1994).

Dong, S., et al., "A New Kind of Chemical Sensor Based on a Conducting Polymer Film," *J. Chem. Soc., Chem. Commun.*, pp 993-995 (1998).

Dong, S., et al., "Chloride Chemical Sensor Based on an Organic Conducting Polypyrrole Polymer," *Analyst*, vol. 113, pp 1525-1528 (Oct. 1988).

Evans, P., et al., "Synthesis and gas sensing properties of poly[tetra (pyrrol-l-yl) silane], " J. Mater. Chem., vol. 6, No. 3, pp 295-299 (1996).

Faverolle, F., et al., "Caractérisation de dépôts adhérents de polypyrrole sur substrats de verre," *J. Chim. Phys.*, vol. 92, pp 943-946 (1995).

Feng, J., et al., "Conformation of polyaniline: effect of mechanical shaking and spin casting," *Synthetic Metals*, vol. 84, pp 131-132 (1997).

Foulds, N.C., et al., "Enzyme Entrapment in Electrically Conducting Polymers," *J. Chem. Socl, Faraday Trans. 1*, vol. 82, pp 1259-1264 (1986).

Fox, M.A., et al., "Covalent Attachment of Arenes to $SnO_2$-Semiconductor Electrodes," *Journal of the American Chemical Society*, vol. 102, No. 12, pp 4029-4036 (Jun. 4, 1980).

Gholamian, M., et al., "Oxidation of Formic Acid at Polyaniline-Coated and Modified-Polyaniline-Coated Electrodes," *Langmuir*, vol. 3, pp 741-744 (1987).

Gorton, L., et al., "Amperometric glucose sensors based on immobilized glucose-oxidizing enzymes and chemically modified electrodes," *Analytica Chimica Acta*, vol. 249, pp 43-54 (1991).

Guiseppi-Elie, A., et al., Proceedings 64th Colloid. and Surf Sci. Symp., Jun. 18-20, 1990, Lehigh Univ., Lehigh PA.

Habib, M.A., et al., "Silanized Polyaniline as an Electrochromech Material," *J. Electrochem. Soc.*, vol. 138, No. 6, pp 1692-1695 (Jun. 1991).

Hoa, D.T., et al., "Biosensor Based on Conducting Polymers," *Anal. Chem.*, vol. 64, pp 2645-2646 (1992).

Hwang, L.S., et al., "A Polymer Humidity Sensor," *Synthetic Metals*, vol. 55, No. 57, pp 3671-3676 (1993).

Imisides, M.D., et al., "Microsensors based on conducting polymers," *Chemtech*, pp 19-25 (May 1996).

Iwakura, C., et al., "Simultaneous Immobilization of Glucose Oxidase and a Mediator in Conducting Polymer Films," *J. Chem. Soc., Chem. Commun.*, pp 1019-1020- (1998).

Kajiya, Y., et al., "Glucose Sensitivity of Polypyrrole Films Containing Immoblized Glucose Oxidase and Hydroquinonesulfonate Ions," *Anal. Chem.*, vol. 63, pp 49-54 (1991).

Karagözler, A.E., et al., "Potentiometric iodide ion sensor based on a conducting poly(3-methylthiophene) polymer film electrode," *Analytica Chimica Acta*, vol. 248, pp 163-172 (1991).

Krutovertsev, S.A., et al., "Polymer film-based sensors for ammonia detection," *Sensors and Actuators B*, vol. 7, pp 492-494 (1992).

Kupila, E.-L., et al., "The effect of silanization and poly (ethylene oxide) on the electropolymerization of pyrrole," *Synthetic Metals*, vol. 62, pp 55-59 (1994).

Kuwabata, S., et al., "Investigation of the gas-transport properties of polyaniline," *Journal of Membrane Science*, vol. 91, pp 1-12 (1994).

Lawrence, A.J., et al., "Conductimetry in Enzyme Studies," *Eur. J. Biohem.*, vol. 24, pp 538-546 (1972).

Liang, W., et al., "Gas Transport in Electronically Conductive Polymers," *Chem. Mater.*, vol. 3, pp 390-391 (1991).

Lu, Z., et al., "Study of $CIO_4^-$-Selective Electrode Based on a Conducting Polymer Polypyrrole," *Electroanalysis*, vol. 1, pp 271-277 (1989).

Ma, Y.L., et al., "Potentiometric selective determination of hydrogen sulfide by an electropolymerized membrane electrode based on binaphthyl-20-crown-6," *Analytica Chimica Acta*, vol. 289, pp 21-26 (1994).

MacDiarmid, A.G., et al., "Secondary doping in polyaniline," *Synthetic Metals*, vol. 69, pp 85-92 (1995).

MacDiarmid, A.G., et al., "Thin films of Conjugated Polymers: Application in Sensors for Hydrocarbon Vapors, Microcontact-Printed Liquid Crystal Displays and Light Emitting Devices," *Polymer Preprints*, vol. 38, No. 1, pp 333-334 (Apr. 1997).

Malmros, M.K., et al., "A Semiconductor Polymer Film Sensor for Glucose," *Biosensors*, vol. 3, pp 71-87 (1987-1988).

Matsue, T., et al., "Electron-transfer from NADH dehydrogenase to polypyrrole and its applicability to electrochemical oxidation of NADH," *J. Electroanal. Chem.*, vol. 300, pp 111-118 (1991).

Matsue, T., et al., "An Enzyme Switch Sensitive to NADH," *J. Chem. Soc, Chem. Commun.*, pp 1029-1031 (1991).

McGill, R.A., et al., "Surface and Interfacial Properties of Surface Acoustic Wave Gas Sensors," *Interfacial Design and Chemical Sensing*, pp 280-294 (1994).

McGovern, M.E., et al., "Role of Solvent on the Silanization of Glass with Octadecyltrichlorosilane," *Langmuir*, vol. 10, No. 10, pp 3607-3614 (1994).

Nishizawa, M., et al., "Electrochemical Preparation of Ultrathin Polypyrrole Film at Microarray Electrodes," *J. Phys. Chem.*, vol. 95, pp 9042-9044 (1991).

Nishizawa, M., et al., "Penicillin Sensor Based on a Microarray Electrode Coated with pH-Responsive Polypyrrole," *Anal. Chem.*, vol. 64, pp 2642-2644 (1992).

Nishizawa, M., et al., "Surface Pretreatment for Electrochemical Fabrication of Ultrathin Patterned Conducting Polymers," *J. Electrochem. Soc.*, vol. 140, No. 6, pp 1650-1655 (1993).

Nishizawa, M., et al., "Ultrathin polypyrrole formed at a twin-microband electrode in the presence of dodecylsulfate," *Journal of Electroanalytical Chemistry*, vol. 371, pp 273-275 (1994).

Onoda, M., et al., "Physical properties and application of conducting polypyrrole-silica glass composite films prepared by electrochemical polymerization," *Synthetic Metals*, vol. 71, pp 2255-2256 (1995).

Oyama, N., et al., *Shinsozai*, vol. 4, pp 56-63 (1993).

Pandey, P.C., et al., "Acetylthiocholine/acetylcholine and thiocholine/choline electrochemical biosensors/sensors based on an organically modified sol-gel glass enzyme reactor and graphite paste electrode," *Sensors and Actuators B*, vol. 62, pp 109-116 (2000).

Partridge, A.C., et al., "High Sensitivity Conducting Polymer Sensors," *Analyst*, vol. 121, pp 1349-1353 (Sep. 1996).

Paschen, S., et al., "Morphology of a conducting polymer and its relation to the electronic properties," *Acta Polymer*, vol. 47, pp 511-519 (1996).

Paul, E.W., et al., "Resistance of Polyaniline Films as a Function of Electrochemical Potential and the Fabrication of Polyaniline-Based Microelectronic Devices," *J. Phys. Chem.*, vol. 89, pp 1441-1447 (1985).

Plueddemann, E.P., Summary of Excerpts from *Silane Coupling Agents*, Plenum Press, New York (1982).

Sun, Z., et al., "Enzyme-Based Bilayer Conducting Polymer Electrodes Consisting of Polymetallophthalocyanines and Polypyrrole-Glucose Oxidase Thin Films," *Anal. Chem.*, vol. 64, pp 1112-1117 (1992).

Temofonte, T.A., et al., "Phthalocyanine semiconductor sensors for room-temperature ppb level detection of toxic gases," *Journal of Applied Physics*, vol. 65, No. 3, pp 1350-1355 (Feb. 1, 1989).

Umaña, M., et al., "Protein-Modified Electrodes. The Glucose Oxidase-Polypyrrole System," *Anal. Chem.*, vol. 58, pp 2979-2983 (1986).

Verghese, M.M., et al., "Electrochemical Growth of Polyaniline in Porous Sol-Gel Films," *Chem. Mater.*, vol. 8, pp 822-824 (1996).

Wei, Y., et al., "Composites of Electronically Conductive Polyaniline with Polyacrylate-Silica Hybrid Sol-Gel Materials," *Chem. Mater.*, vol. 7, pp 969-974 (1995).

Wrighton, M.S., et al., "Preparation of Chemically Derived Platinum and Gold Electrode Surfaces. Synthesis, Characterization, and Surface Attachment of Trichlorosilylferrocene, (1,1'-Ferrocenediyl) dichlorosilane, and 1,1'-Bis (triethoxysilyl) ferrocene," *Journal of the American Chemical Society*, vol. 100, No. 23, pp 7264-7271 (Nov. 8, 1978).

Wu, C.-G., et al., "Chemical Deposition of Ordered Conducting Polyaniline Film via Molecular Self-Assembly," *Chemistry of Materials*, vol. 9, No. 2, pp 399-402 (Feb. 1997).

Yamagishi, F.G., et al., "Conductive Polymer-based Sensors for Application in Nonpolar Media," *Polym. Mater. Sci. Eng.*, vol. 71, pp 656-657 (1994).

Yamagishi, F.G., et al., "Conductive Polymer-based Transducers as vapor-phase detectors," *Proc. of the SPE Annual Technical Conference and Exhibits*, ANTEC 98, XLIV, pp 1335-1339 (1998).

Yamagishi, F.G., et al., "Enhanced Stability, Reversibility and Sensitivity of Conductive Polymer-Based Volatile Organic Compound Sensors," *Electrochemical Society Proceedings*, vol. 97, No. 19, pp 103-108 (1997).

Yang, X.Q., et al., "Poly(heterocycle) Langmuir-Blodgett Films," *Langmuir*, vol. 5, pp 1288-1292 (1989).

Abstract of Flounders, A.W., et al., "Development of Sensors for Direct Detection of Organophosphates," *Biosensors and Bioelectronics*, Retrieved on Apr. 14, 2005, pp. 1-2 (Dec. 1999).

"Enzymatic Reaction of Organophosphate Hydrolase," INTERNET: <http://www.reactivesurfaces.com/rs_news/ wp_enzymatic_reaction.html> Retrieved on Apr. 14, 2005, 1 page total (2003).

"Glucose Oxidase: A Much Used and Much Loved Enzyme in Biosensors," INTERNET: <http://www-biol.pasiley.ac.uk/marco/enzyme_electrode/chapter3/chapter3_page1.htm> pp. 1-2 (Retrieved on Apr. 19, 2005).

Leboffe, M.J., et al., *A Photographic Atlas for the Microbiology Laboratory*, Second Edition, Morton Publishing Company, p. 76 (1999).

Leboffe, M.J., et al., *A Photographic Atlas for the Microbiology Laboratory*, Second Edition, Morton Publishing Company, p. 44 (1999).

Prescott, L.M., et al., *Microbiology*, Brown & Benchmark, p. 178-179 (1990).

Prescott, L.M., et al., *Microbiology*, Brown & Benchmark, pp. 333-335 (1990).

Silverman, R.B., *The Organic Chemistry of Enzyme Catalyzed Reactions*, Academic Press, p. 193 and p. 195 (2002).

*The New Lexicon Webster's Dictionary of the English Language*, Lexicon Publications, Inc., New York, p. 735 (1988).

\* cited by examiner

SENSORS WITH VARIABLE RESPONSE BEHAVIOR

CROSS-REFERENCE TO RELATED APPLICATIONS

This application claims priority under 35 U.S.C. §119(e) to co-pending U.S. Patent Application No. 60/316,111 (filed Aug. 29, 2001) entitled "Stabilized Conductive Polymer/ Bioindicator Sol-gel Sensors with Variable Response Behavior," the contents of which are hereby expressly incorporated herein in their entirety by this reference.

This application also is a U.S. continuation-in-part of co-pending PCT International Patent Application No. PCT/US01/28717 (filed Sep. 10, 2001 and designating the United States) entitled "Sensor for Chemical and Biological Materials," the contents of which are hereby expressly incorporated herein in their entirety by this reference.

In addition, this application is a U.S. continuation-in-part of U.S. patent application Ser. No. 09/679,428 (filed 3 Oct. 2000) now U.S. Pat. No. 6,730,212 entitled "Sensor for Chemical and Biological Materials," the contents of which are hereby expressly incorporated herein in their entirety by this reference.

I. BACKGROUND OF THE INVENTION

1. Field of the Invention

This invention relates to the field of biological indicators and sensors for detecting certain harmful chemical and/or biological agents. More particularly, it pertains to the use of a chemical and/or morphological change in the material of the sensor when a target pathogen or vapor interacts with the sensor. The sensor is inexpensive, sensitive, selective, robust, and covertly deployable.

PCT International Publication No. WO 02/29378 A2 (published on Apr. 11, 2002) is entitled "Sensor for Chemical and Biological Materials," the contents of which are hereby expressly incorporated herein in their entirety by this reference.

2. Description of the Related Art

The need for detection of chemical and/or biological agents in a variety of applications is acute. In attempts to satisfy this need, the development of biosensors has been a particularly active field in recent years, resulting in numerous concepts and devices. A substantial amount of prior art has been generated by various researchers working in this field and a number of methods have been developed which allow such detection. The most important results of such prior art are discussed below. However, none of the methods described in the prior art is quite acceptable, as subsequently discussed. See, for instance:

(1) B. C. Dave, B. Dunn, J. S. Valentine, and J. T. Zink, *Anal. Chem.* 1994, 1120A–1127A.

The approaches developed in the prior art typically use encapsulation of enzymes, antigens and/or antibodies in sol-gel matrices as a means of stabilizing their biochemical activity and providing a means to react with smaller molecules that diffuse through the pores of the gel.

Such techniques have typically been applied to immunoassay techniques, but characteristically involve aqueous based chemistry with electrochemical and/or optical methods of detection. These techniques are usually not real-time. Other approaches to airborne sensing of biomaterials are also available, including mass spectrometry and infrared spectroscopy, but these methods are complex, costly and not readily amenable to covert or continuous, unattended monitoring.

The concept of immobilizing indicator biomolecules onto conductive polymer substrates, i.e., by encapsulation, as well as the development of chemical and biological sensor devices that are based on electroconductive polymers in general, is an area that has attracted considerable recent attention. See, for instance:

(2) A. Guiseppi-Elie, U.S. Pat. No. 5,766,934;

(3) M. Umana and J. Waller, *Anal. Chem.* 1986, 58, 2979–2983;

(4) N. C. Foulds and C. R. J. Lowe, *Chem. Soc., Faraday Trans.* 1, 1986, 82, 1259–1264;

(5) C. Iwakura, Y. Kajiya and H. Yoneyama, *J. Chem. Soc., Chem. Commun.* 1988, 15, 1019;

(6) T. Matsue, et. al. *J. Electroanal. Chem. Interfacial Electrochem.*, 1991, 300, 111–117;

(7) M. Malmors, U.S. Pat. Nos. 4,334,880 and 4,444,892;

(8) M. K. Malmors, J. Gulbinski, III, and W. B. Gibbs, Jr. *Biosensors,* 1987/88, 3, 71.

However, all of the electroactive biosensors described in the above-mentioned publications are designed to operate in aqueous environments, not in air. The present invention, as subsequently discussed, not only allows for the detection of the chemical and/or biological agents in aqueous environments, but it also has the further advantage of detecting these agents in gaseous environments, such as air, as well.

The present invention applies the concept of using indicator biological materials (hereinafter, biomaterials or biomolecules) for such detection as these biomaterials are first ensconced on electroconductive polymer carriers.

In general, these devices are formed from thin films of electroconductive polymer fabricated on a pattern of microsensor electrodes, which are, in turn, formed on an insulating substrate. Sensor devices that exploit the transducer-active responses of electroactive polymers may be conductometric, as discussed, for example, in:

(9) A. J. Lawrence and G. R. Moores, *Eur. J. Biochem.* 1972, 24, 538–546;

(10) D. C. Cullen, R. S. Sethi and C. R. Lowe, *Anal. Chim. Acta* 1990, 231, 33–40.

A number of ways to cause the transducer-active conductometric response has been described. The prior art teaches the use of the large change in electrical impedance for that purpose. See, for example:

(11) A. Guiseppi-Elie and A. M. Wilson, Proceedings 64th Colloid. and Surf Sci. Symp., Jun. 18–20, 1990, Lehigh University, Lehigh, Pa.;

(12) T. Matsue, et. al., *J. Chem. Soc., Chem. Commun.* 1991, 1029–1031;

(13) M. Nishizawa, T. Matsue and I. Uchida, *Anal. Chem.* 1992, 64, 2642, 2644;

(14) D. T. Hoa, et. al., *Anal. Chem.* 1992, 64, 2645–2646;

(15) Guiseppi-Elie, A. U.S. Pat. No. 5,312,762;

A conductometric response that accompanies oxidation and/or reduction of the polymer, the amperometric response, has also been described. See, for example:

(16) L. Gorton, et. al., *Anal. Chim. Acta* 1991, 249, 43–54.

The use of redox mediation and/or electrocatalysis to cause the transducer-active conductometric response has been also described. See, for example:

(17) M. Gholamian, et. al., *Langmuir,* 1987, 3, 741;

(18) Y. Kajiya, et. al., *Anal. Chem.* 1991, 63, 49;

(19) Z. Sun and H. Tachikawa, *Anal. Chem.* 1992, 64, 1112–1117.

In particular, the potentiometric method, when the electrode potential change that accompanies changes in polymer redox composition is measured, was used. See, for example:

(20) S. Dong, Z. Sun, and Z. Lu, *J. Chem. Soc., Chem. Commun.* 1988, 993;

(21) S. Dong, Z. Sun, and Z. Lu, *Analyst*, 1988, 113, 1525;

(22) Z. Lu, Z. Sun and S. Dong, *Electroanalysis*, 1989, 1, 271;

(23) A. E. Karagozler, et. al., *Anal. Chim. Acta*, 1991, 248, 163–172;

(24) Y. L. Ma, et. al., *Anal. Chim. Acta* 1994 254 163–172.

As will be shown below, the detection of the chemical and/or biological agents in accordance with one aspect of the present invention measures transducer-active conductometric response as a result of a morphological as well as chemical change in a polymer film.

A morphological change results when the target chemical or biological agent is absorbed into and retained within the gel as a result of its interaction with the bioindicator. The gel must swell (being somewhat flexible due to its hydrated state) to accommodate this absorbed material, causing the embedded conductive polymer molecules to separate relative to each other, causing a decrease in overall conductivity.

None of the prior art mentioned above teaches or discloses the measurement of the conductometric response as a result of a morphological change.

Furthermore, conductive polymer based sensors have been developed for detecting volatile organic compounds in air, along with chemical weapon simulants. See, for example:

(25) F. G. Yamagishi, et al., Proc. of the SPE Annual Technical Conference and Exhibits, ANTEC 98, XLIV, 1335 (1998).

Other sensor technologies include surface acoustic wave devices (which require complex frequency counting electronics), mass spectroscopy, infrared spectroscopy, and gas chromatography, or some combination or combinations of these methods. These techniques are currently being developed but are primarily directed toward laboratory analysis rather than field application. All of the existing methods of analysis and detection of biological pathogens and chemical agents have serious disadvantages of having large size, long analysis times, complicated electronics support, lack of specificity and/or high cost.

In view of the foregoing, there is a need for a simple, inexpensive and accurate sensor for detection of biological pathogens and chemical agents. A sensor is needed which is also low power, compact, rugged, highly selective, and adaptable to field application for detection of vapor phase pathogens in real time without the need for involving "wet" chemistry. There is no known prior art which teaches a sensor satisfying all these requirements.

A principle that biological materials can be detected by detecting changes in indicator materials due to their interaction through highly specific processes is frequently exploited as a means of determining their presence in various media, under airborne or aqueous scenarios. This invention utilizes this principle and provides for a rugged, low-cost, highly sensitive and selective sensing device suitable for remote real-time covert field monitoring and detecting of relevant biomaterials.

Previously, a biosensor was demonstrated based on the conjugate glucose oxidase/glucose, where the enzyme was encapsulated in a sol-gel matrix, which was in turn coupled with a conductive polymer. This biosensor is described in U.S. Pat. No. 6,730,212, filed on Oct. 3, 2000. In principle, the approach described in U.S. Pat. No. 6,730,212 is applicable to numerous types of bioindicator molecules.

This approach provides for high specificity as well as enhanced stability of the enzyme, since it is physically confined (preventing denaturing) and the aqueous environment and pH necessary for vitality are also included in the pore. The present invention will enhance and enable this concept to meet specific sensing applications.

Such enhancement and fine tuning of the invention described in U.S. Pat. No. 6,730,212 is necessary because it was observed that such encapsulated bioindicators are very sensitive to the chemical and physical properties of certain co-encapsulated conductive polymers such as, for instance, polyaniline sulfonic acid. The technique of this invention provides a means by which this problem may be minimized or avoided.

In particular, the sensor described in U.S. Pat. No. 6,730,212 turned out to be insufficient when the encapsulated bioindicator is a very important enzyme acetylcholinesterase (AChE), described subsequently in detail.

The present invention provides a sensor by combining conductive polymer transducers and encapsulated sol-gel techniques and makes this approach usable even for highly labile enzymes. The combination of these approaches is not found in any other sensor device for the detection of biological or chemical materials.

II. SUMMARY OF THE INVENTION

In the present invention, a bioindicator material is ensconced within an inorganic sol-gel glass film incorporating a conductive polymer. The conductivity of the polymer is maintained after the bioindicator has been embedded, while the stability of the bioindicator is preserved intact. Typically, a bioindicator is encapsulated in a sol-gel film to provide the proper pH and nutrients necessary for viability of the bioindicator.

As mentioned above, the enzyme AChE is crucial in selective biological processes and therefore serves as an important bioindicator material. However, prior attempts at preparing active gels of AChE using the encapsulation procedures developed before (i.e., encapsulating the enzyme directly in a sol-gel matrix coupled with a conductive polymer) proved unsuccessful because of the high lability of AChE and its consequent tendency to readily denature in the presence of conductive polymers. The present invention overcomes this problem.

As a result, stable formulations of a conductive polymer and AChE have been prepared and used to demonstrate transduction between this encapsulated enzyme and the conductive polymer using airborne cholinesterase inhibitors. To achieve such result, a bioindicator is sandwiched between two sol-gel layers, in one of which a conductive polymer is first incorporated. In this manner, the bioindicator is protected from denaturation by the conductive polymer.

A similar approach is used in a sensor reported by Pandy et. al., “Acetylthiocholine/acetylcholine and thiocholine/choline electrochemical biosensors/sensors based on an organically modified sol-gel glass enzyme reactor and graphite paste electrode,” Sensors and Actuators B, 62 (2000) 109–116. In this report, mixtures of 3-aminopropyltriethoxysilane (3-APTES) and 2-(3,4 epoxycyclohexyl) ethyltrimethoxysilane (EETMS) proved to be successful in providing active and well-adhered films containing an AChE immobilized enzyme they report is relatively stable.

The top and bottom sol-gel layers in Pandy were designed to be permeable to acetylcholine/acetylthiocholine, and the rate of hydrolysis of these materials was used by Pandy to determine AChE activity in an aqueous environment.

However, the Pandy approach has a major drawback in that it is not well suited for the rapid determination of AChE inhibitors in air.

In the present invention, a conductive polymer is incorporated into the bottom layer of the sandwich and is used to directly monitor the activity of the bioindicator applied to the surface of this layer. This invention, in contrast to Pandy's method, allows for the direct determination of airborne cholinesterase inhibitors.

A top layer sol-gel film is also used, which is specifically formulated to provide the porosity necessary for permeation of analytes. Despite its porous nature, the top layer sol-gel film protects the bioindicator from denaturation by effect of the environmental factors. In this manner a stable and active immobilized bioindicator composite film is formed, which is useful as a transducer for sensing airborne pathogenic materials.

This top layer may be applied as a cover layer over the bioindicator, or alternately this top layer may be formulated to contain the bioindicator, suitably incorporated therein. Similarly, the porosity of the top layer sol-gel allows permeation of the target analyte(s), while providing a secure environment for the bioindicator.

Furthermore, in this invention the sol-gel film may be formulated to control the state of doping of the conductive polymer. By using sol-gel precursors which selectively dope or de-dope the conductive polymer, the electronic makeup of the polymer may be adjusted, thereby altering its response mechanism. Consequently, composite transducer films may be formed using different sol-gel formulations incorporating the same bioindicator and conductive polymer, but whose responses to a given analyte are very different.

In addition, it is important to note that sensors based on interactions specific for a biomaterial are desirable because of their high selectivity for detection. However, it is known to those skilled in the art that such bioindicators are frequently more susceptible to denaturation as they become more specific in their interactions and more relevant to higher-order mammalian processes. Furthermore, each different analyte requires a new bioindicator and preparing useful and active films often becomes an expensive time and labor consuming undertaking. The ability to use less specific biomaterials provides an attractive alternative to this approach due to their higher degree of stability and for economic reasons.

This invention provides such methods allowing for variation in the response behavior of the transducers. For example, AChE interacts with a select class of materials (i.e. cholinesterase inhibitors) which include several important analytes. Once an approach for stabilizing sol-gel films of AChE has been developed, it would be useful to use this same bioindicator to speciate between several cholinesterase inhibitors.

By generating varied responses from the same bioindicator, different formulations will give rise to different response signals, providing the means to discriminate between similar analytes and to reject interferences resulting in fewer false alarms. Such a variable response behavior makes possible the use of arrays and the application of pattern recognition techniques for speciation.

While, as mentioned above, the typical approach to using bioindicators for detection of biomaterials is based on the high specificity of the interaction between target and substrate, this invention provides a means of generating a specific response from a small number of specific bioindicators.

Instead of trying to solve the often insurmountable task of developing stable formulations for new and increasingly labile bioindicators for each target analyte, this invention first provides for preparation of stable films of a class-specific bioindicator, followed by speciation amongst members of this class by making small changes in the film formulation.

In accordance with one aspect of this invention, a sensor for detecting pathogens in the air is provided, the sensor comprising a dielectric substrate, interdigitated electrodes attached to the substrate, a conductive polymer-containing film applied over the interdigitated electrodes, an indicator biomolecule incorporated within the film, and an instrument to measure an electric current flowing through the conductive polymer.

In accordance with another aspect of this invention, a method for detecting pathogens in the air is provided, the method comprising steps of disposing a plurality of interdigitated electrodes on a dielectric substrate, applying a conductive polymer-containing film over the interdigitated electrodes, incorporating an indicator biomolecule into the film by imbedding the indicator biomolecule within the film or attaching the indicator biomolecule to the film, exposing the film to the environment containing the pathogens, applying an electric voltage to the interdigitated electrodes, and measuring a change in an electric current flowing through the conductive polymer, the change being caused by interaction of the pathogens with the film.

According to yet another aspect of this invention, the indicator biomolecules proposed to be used comprise enzymes, and in particular, organophosphate hydrolase, cholinesterase, acetylcholinesterase, catalase, $\alpha$-amylase and or superoxide dimutase. The pathogens to be detected comprise enzyme substances and inhibitors of enzymes, in particular, acetylcholine, organophosphorous compounds, thiophosphorous compounds, hydrogen peroxide, and organic peroxides.

III. BRIEF DESCRIPTION OF THE DRAWINGS

The features and advantages of the present invention will become better understood with regard to the following description, appended claims, and accompanying drawings.

IV. DETAILED DESCRIPTION OF THE INVENTION

The sensor which is the subject matter of the present invention preferably comprises a conductive polymer transducer and indicator biomolecules encapsulated in a sol-gel-derived material.

1. The Sensor in General

Figure 1:
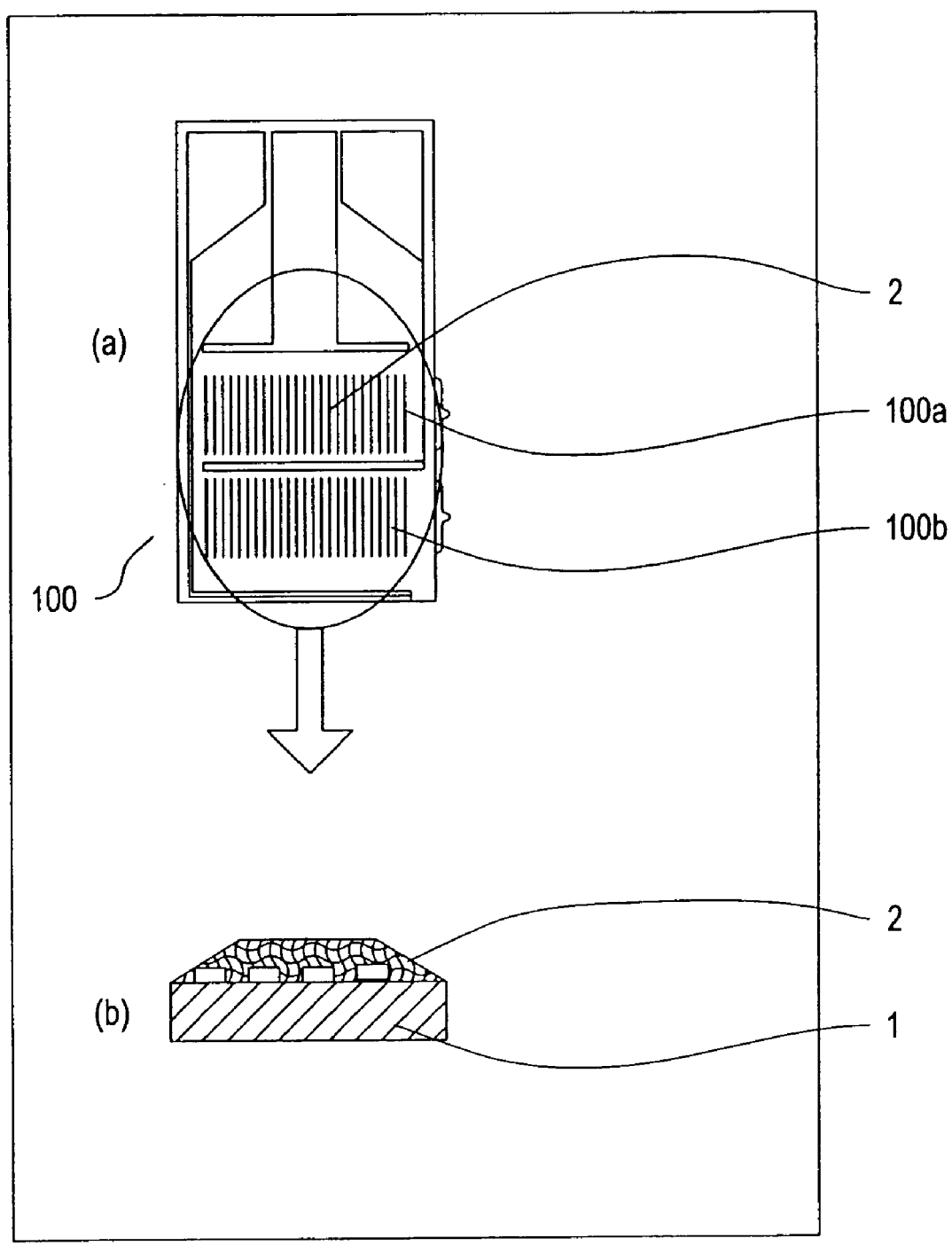
FIG. 1 is schematic diagram showing an elevation view (a) of the sensor and a top view of the architecture of the sensor (b).

FIG. 1 schematically illustrates two views of the sensor of this invention. FIG. 1(a) shows schematically the structure of an embodiment of the sensor 100. Generally, one sensor element is present on a dielectric substrate 1, but more than one sensor can be present in a particular assembly. For example, FIG. 1(b) shows a dielectric substrate 1, which can be commercially available (for instance, from ABTECH Scientific of Richmond, Va.) and which contains two sensor elements 100a and 100b combined in one assembly to be subsequently discussed. Such a two sensor element assembly was used for tests discussed hereinafter.

Two identical sensor elements can be provided in one assembly, or two separate sensor elements can be utilized. In such case one would preferably be used for measurements while the other sensor will preferably act as a reference. A sensor element containing only one sensor, and, therefore, only one set of subsequently discussed interdigitated electrodes is completely acceptable and adequate in some embodiments. Those skilled in the art will determine the number of sensors used in the assembly, and which number should be suitable for a particular use.

Metal interdigitated electrodes 2 are deposited on a dielectric substrate 1. A material of which dielectric substrate 1 is made comprises any dielectric material, such as quartz, glass, ceramic, or plastic. The choice of a particular substrate will be made by those skilled in the art according to the needs of a particular application. The thickness of the dielectric substrate 1 ranges from preferably about 5 micrometers (in case a plastic is used as the dielectric substrate 1) to preferably about 2 millimeters (in case of a glass or ceramic dielectric substrate 1).

Figure 3:
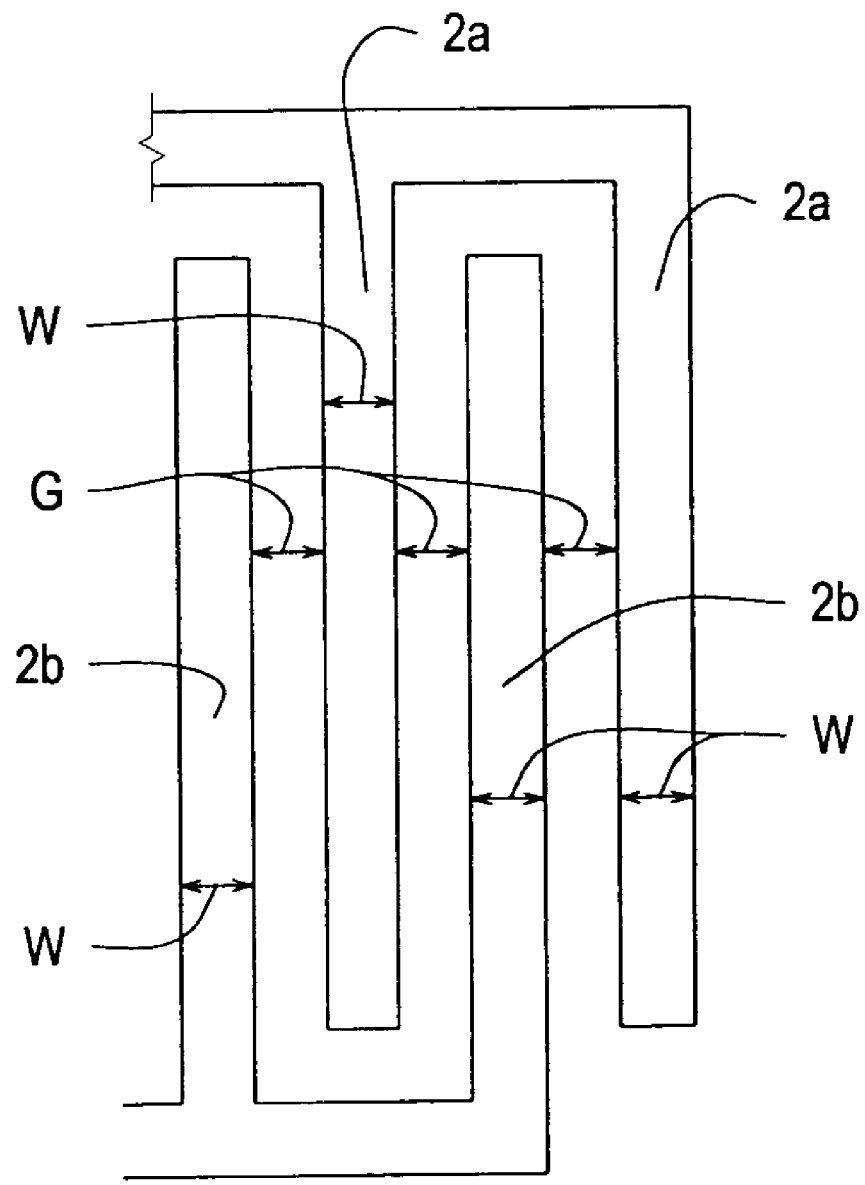
FIG. 3 is a schematic diagram showing a plan view of the electrodes when viewed along the 2—2 line of FIG. 2

Interdigitated electrodes 2, comprising first and second sets of digits 2a and 2b, are made of any material conducting electricity, but preferably are made of gold, due to gold's good conductivity and general inert nature. Modulation of the conductivity of a circuit comprising digits 2a and 2b, upon which detection of biological and/or chemical materials depends, is accomplished by a modification of the morphology of the material in the gaps G between the digits 2a and 2b (see FIG. 3).

It is necessary for proper operation of the sensor to fill gaps G uniformly and to obtain a sufficiently strong electrical signal. The electrode configuration shown in FIGS. 1 and 3, and described below, is adequate in order to be able to both achieve the uniformity of the film G and to obtain a sufficiently strong electrical signal.

The shape of the electrodes 2 is preferably rectangular in cross section. As mentioned above, each electrode 2 comprises a plurality of digits 2a and 2b, the digits interleaving as shown on FIG. 3. The width W of each digit 2a and 2b is within a range of between about 5 micrometers and about 25 micrometers, preferably about 15 micrometers. The gaps G between the digits 2a and 2b are within a range of between about 5 micrometers and about 25 micrometers, preferably about 15 micrometers.

Figure 2:
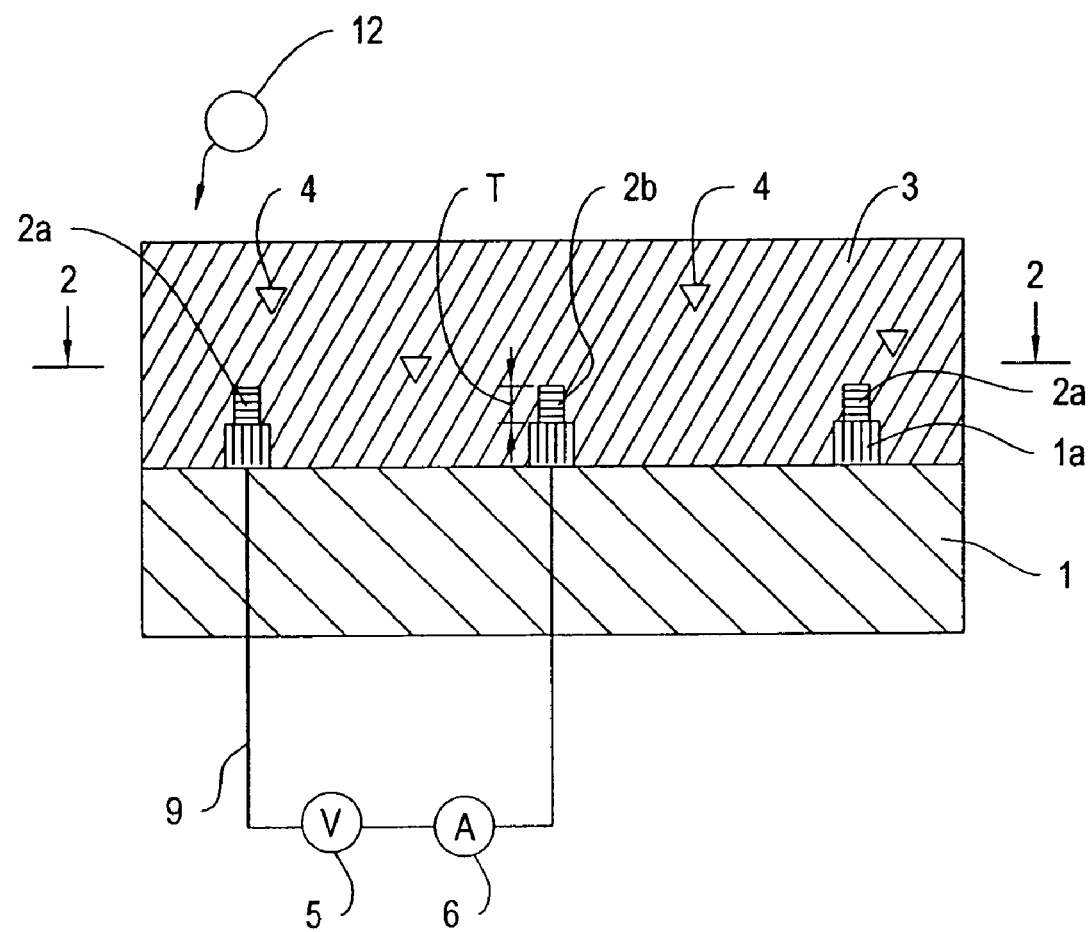
FIG. 2 is a schematic diagram showing parts of the sensor.

The thickness T of each digit 2a and 2b is within a range of about 1 micrometers to about 4 micrometers, as shown on FIG. 2. About 50 line pairs of digits 2a and 2b are preferably used, but the number of such line pairs can vary with the application and the dimensions of the sensor element required for a particular application.

The electrode pattern described above and shown in FIGS. 1 and 3 is made by standard semiconductor processing techniques known to those skilled in the art. For example, a clean glass substrate 1 (FIG. 2) is coated with a thin layer of titanium or titanium/tungsten alloy 1a, preferably by sputtering. This layer 1a, the thickness of which is preferably about 100 Angstroms, acts as an adhesion layer for the gold electrode. The next step is deposition of a layer of gold having a thickness within a range of between about 1 micrometer and about 4 micrometers, either by sputtering or evaporation.

A photoresist (not shown) is applied to the bilayer thus formed, which photoresist is patterned to the desired electrode configuration using a lithographic mask (not shown). Once the pattern is formed by the photoresist, the gold is removed from the substrate by etching away the gold and layer 1a, preferably by sputter etching, after which the resist is removed leaving the complete set of highly adhering interdigitated electrodes 2 disposed on the remainder of the thin layer of titanium or titanium/tungsten alloy 1a.

The electrodes 2 are coated with a thin composite film 3 comprising a conductive polymer component to be discussed in detail subsequently. Previously, it was disclosed that the electrodes 2 are coated with a thin composite film 3 comprising a conductive polymer component and a sol-gel-derived material component (see, U.S. Pat. No. 6,730,212).

However, some enzymes and some other biospecific materials are known to be very sensitive to the chemical and physical properties of the co-encapsulated conductive polymers. This is so because some enzymes and some other bioindicators are highly unstable and prone to denaturation in an unprotected environment.

Therefore, even though encapsulation in sol-gel glasses has been generally shown to be an effective means of stabilizing such materials, by providing the proper pH, water and other nutrients, and preventing the enzyme from uncoiling or denaturing, the co-encapsulation of the key enzyme AChE with conductive polymers in sol-gel glass according to a method described in U.S. Pat. No. 6,730,212 does not achieve such stabilization because AChE has an increased lability and enhanced propensity to denature. This invention proposes a new technique to be used for AChE and other similarly labile enzymes or other labile bioindicators.

This invention provides a means of preparing stable, adherent, and active films of labile enzymes with incorporated conductive polymers.

2. A Preferred Embodiment of the Sensor

Figure 4A:
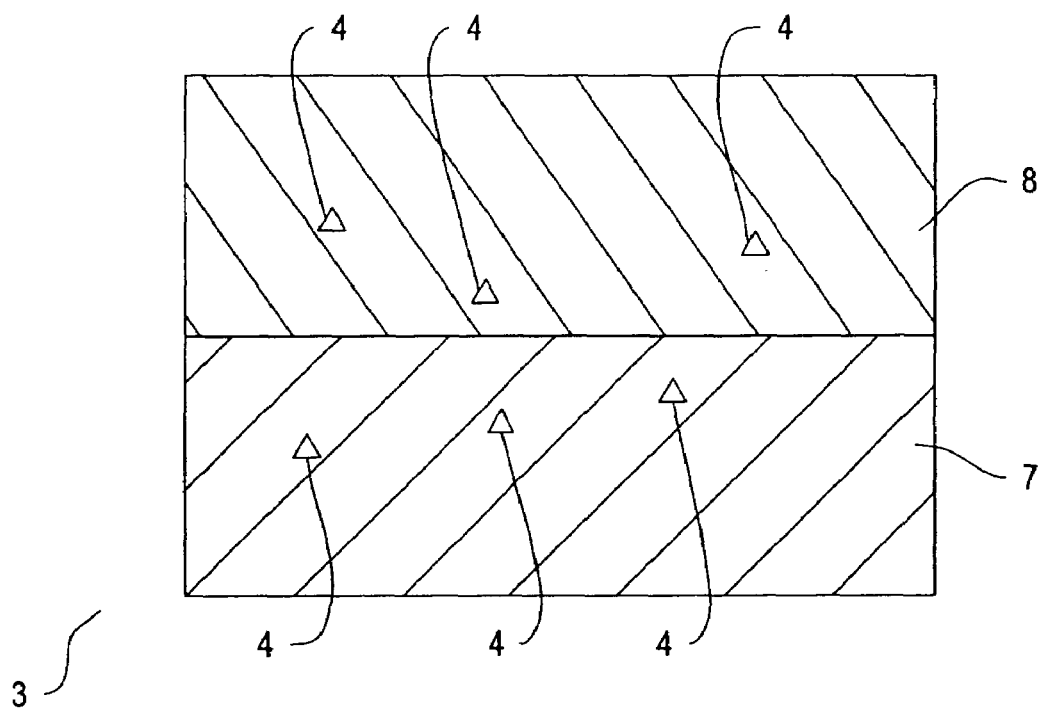
FIG. 4a is a schematic diagram showing the internal structure of a portion of a preferred embodiment of the sensor in more detail.

As shown on FIG. 4a, the thin composite film 3 (with which the electrodes 2 are coated), in a preferred embodiment, comprises two sol-gel ingredients 7 and 8, and the bioindicator material 4 incorporated in the film 3 and distributed between the ingredients 7 and 8. The thickness of composite film 3 is within a range of between about 100 micrometers and about 1,000 micrometers, preferably within a range of between about 100 micrometers and about 300 micrometers.

A preferred bioindicator material 4 is the enzyme acetylcholine esterase (AChE) (Sigma Chemical Co. of St. Louis, Mo.), to be discussed below in greater detail. It is incorporated in a buffer solution so as to achieve a slightly basic environment having a pH of about 8. The buffer is a commonly used buffer solution, the choice of which is known to those skilled in the art.

A number of alternative bioindicators can be used as well, including other enzymes, for example, glucose oxidase, α-amylase, catalase, superoxidase dimutase, L-asparaginase, glutamate dehydrogenase, and organophosphate hydrolase. Other classes of alternative bioindicators can be used, including antibodies, for example, *escherichia coli* serotype 157:H7 IgG, goat anti-human IgG(γ), goat anti-*bacillus anthracis antisera,* and anti-TNT IgG; deoxyhemoglobin; and antibiotics; for example, penicillin G or methicillin (naficillin or oxacillin). This list of the alternative bioindicators is not exhaustive, and those skilled in the art will choose other bioindicators having similar properties.

The sensor of this invention is as well suited for any of these bioindicators as for AChE of the preferred embodiment. Each of these alternative bioindicators is sensitive to particular classes of pathogens, which pathogens are inhibitors of, or in other ways interact with, corresponding enzymes, antibodies or antibiotics. The pathogens inhibiting, or in other ways interacting with, particular classes of bioindicators are known to those skilled in the art.

The ingredient 7 preferably comprises a blend of preferably 2-(3,4-epoxycyclohexyl)ethyltrimethoxysilane (EETMS) (United Chemical Technologies, Inc. of Bristol, Pa.), and having the formula (1)

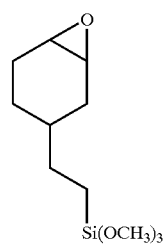

(1)

with preferably 3-aminopropyltriethoxysilane (3-APTES) (Sigma Chemical Co. of St. Louis, Mo.), and having the formula (2):

$$NH_2-CH_2-CH_2-CH_2-Si(OC_2H_5)_3 \quad (2),$$

with preferably about 10% by weight (of the entire ingredient 7) of preferably polyaniline sulfonic acid (PAS) (Nagase America Corporation of New York, N.Y.). Other suitable conductive polymers, for instance, polyaniline, polythiophene, polypyrrole, or their derivatives, can be selected according to criteria known to those skilled in the art.

Instead of the above-mentioned, preferred silanes, other silanes can be used, such as trifunctional silanes, for instance, methyltrimethoxysilane, octadecyltrichlorosilane, octadecyltriethoxysilane, phenyltrimethoxysilane, or 1,4-bis(trimethoxysilylethyl)benzene. Mono- or difunctional silanes, for example, octadecyldimethylmethoxysilane, methyldimethoxysilane, or dimethyldiethoxysilane can also be used. Finally, some derivative silanes can be used as well, including, for example, 2-(3,4-epoxycyclohexyl)ethyltrimethoxysilane, 3-aminopropyltrimethoxysilane, 4-aminobutyldimethylmethoxysilane, dicyclohexyldimethoxysilane, N-(2-aminoethyl)-3-aminopropylmethyldimethoxysilane, 5-(bicycloheptenyl)triethoxysilane, 3-glycidylpropyltrimethoxysilane, or silanes having similar properties.

Those skilled in the art will choose a pair of silanes to form a bi-ingredient film 3 having the properties needed according to the design. The ratios between various silanes are generally about 1:10, and in the preferred embodiment the ratio between EETMS and 3-APTES is between about 1:1 and about 1:10, preferably, about 1:3.5 (by weight).

PAS is dissolved in water. The resulting solution of PAS is then mixed with 3-APTES and EETMS, described above, to form a final conductive hybrid material following the evaporation of the solvent and gelation.

The polyaniline-based conductive polymer forms an interpenetrating type of three-dimensional network throughout the ingredient 7. Thus, the conductive polymer is intimately intertwined throughout the ingredient 7, and therefore available to interact with any species (i.e., reaction products from the interaction of bioindicator and substrate) which may be present, and is also capable of detecting any changes to the structure of the sol-gel film 3.

It is also important that the conductive polymer incorporated in the ingredient 7 not provide any species which may migrate to the bioindicator 4 and cause its denaturation. The conductive polymer counterions are known to be able to cause such denaturation. Therefore, a conductive polymer such as PAS should be used because the migration of the polymer counterions into the middle layer containing bioindicator 4 is precluded since the sulfonate counterion is covalently bound to the polyaniline backbone and subsequent denaturation of the enzyme is prevented.

The ingredient 8, the use of which is optional, preferably comprises a blend of EEMTS and 3-APTES. The presence of the sub-layer 8 is optional, as discussed below. The film 3 is prepared by combining ingredient 7, the bioindicator, and, optionally, ingredient 8 in a fluid form, and allowing the blend to naturally solidify.

The preferred bioindicator material 4 is chosen to be AChE because this is an enzyme critically important for certain functions in the human body, and is therefore an excellent indicator of certain classes of pathogenic materials, such as cholinesterase inhibitors. AChE, enzyme number 3.1.1.7, according to the EC-classification, acts on a variety of acetic esters and catalyzes transacetylations.

AChE is particularly important for catalyzing the hydrolysis of acetylcholine($CH_3$)$_3$N$^+$($CH_2$—$CH_2$—OCO—$CH_3$) OH$^-$(trimethyl($\beta$-acetyl)-ammonium hydroxide) to choline ($CH_3$)$_3$N$^+$$CH_2$—$CH_2$OH$^-$(trimethyl($\beta$-hydroxyethyl)ammonium) and acetate. If the activity of AChE is suppressed or inhibited, the above-mentioned reaction of hydrolysis is either severely slowed down or even does not occur at all. As a result, a very rapid accumulation of unhydrolyzed acetylcholine takes place with extremely negative consequences for health and even life itself, such as paralysis of the nerve centers.

When a sensor comprising the film 3 in which AChE (the bioindicator 4) is ensconced, is exposed to a media containing an inhibitor of AChE, the latter is inhibited as a result of a chemical reaction between this inhibitor and AChE. The inhibitors of AChE are known to be certain derivatives of phosphoric, thiophosphoric, and phosphonic acids.

Such chemical reactions between AChE and an inhibitor may take place, when AChE comes into contact with some insecticides, e.g, malathion, S-(1,2-dicarbethoxyethyl)-O,O-dimethyldithiophosphate, or parathion, diethyl-p-nitrophenylmonothiophosphate, as shown below (reactions 3 and 4, respectively).

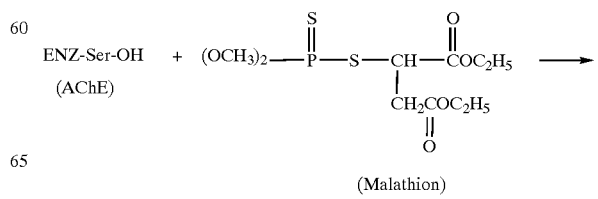

(Malathion)

-continued

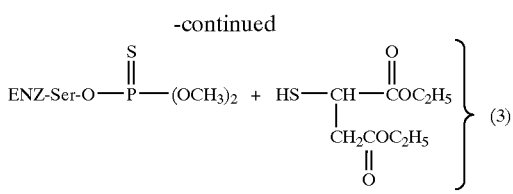
(3)

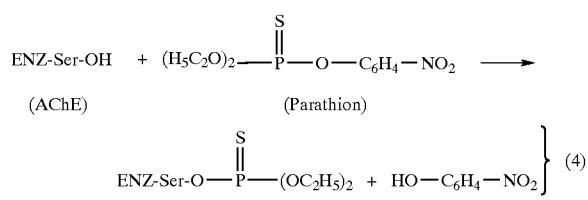
(4)

As can be seen from reactions (3) or (4), an esterified thiophosphate group attaches itself to the enzyme, via a serine bridge, suppressing the enzyme's ability to catalyze the hydrolysis of acetylcholine.

These or similar (if other phosphates, thiophosphates, or phosphonates play a role of an inhibitor) reactions will produce chemical by-products and/or a change in the volumetric size of the enzyme With this arrangement, transduction of the interaction between bioindicator 4 and pathogenic analyte (such as malathion or parathion shown above or other phosphate, thiophosphate, or phosphonates) can result either through permeation of the chemical by-products or through any changes in molar volume of the bioindicator 4 that may occur.

Volumetric changes in film 3, with the bioindicator AChE 4 embedded therein, similarly cause specific and characteristic distortions of the ingredient 7 of the film 3, the ingredient comprising the conductive polymer component The formation of by-products is even a more significant phenomenon. Chemical by-products of reactions (3) or (4) or similar reactions will cause either redox processes within the conductive polymer component of ingredient 7 or result themselves in morphological changes in the film 3, thereby modulating the conductivity of the polymer component of the ingredient 7. Different by-products will generate different response behavior for a given conductive polymer, thus allowing sensing and detection.

AChE needs to be in proximity to the conductive polymer component in order to allow the changes in AChE caused by the reactions described above to be detected. When AChE is directly encapsulated with many conductive polymers, it easily denatures and becomes inactive. In this invention, by separating the AChE bioindicator 4 from the conductive polymer of the ingredient 7, chemical denaturation of the AChE bioindicator 4 by the conductive polymer is avoided, thereby making the sensor of this invention viable. Thus incorporating the conductive polymer in the ingredient 7 of film 3, the AChE bioindicator 4 is protected, while it still interacts with the conductive polymer component.

3. The Operation of the Sensor

The sensor 100, as shown on FIG. 1, is equipped with a source of voltage 5 and an ammeter 6, shown on FIG. 2. When a pathogenic analyte 12 to be detected, i.e., an organophosphate, thiophosphate or phosphonate described above, approaches the sensor 100, it interacts with the AChE bioindicator 4 causing morphological changes in the thin composite film 3. These changes in turn modulate the conductivity of the conductive polymer component in the ingredient 7 of the thin film 3. As a result, a change in the electrical current in circuit 9 is registered by the ammeter 6.

The sensor elements 100a and 100b are monitored by applying a voltage and reading out the change in current. The voltage can be applied by a nominal power supply (e.g., external or designed into circuitry, or a battery). Both alternating and direct current sources are acceptable. Similarly, the output current can be monitored by an external ammeter or one designed into the circuitry. Electronic designs in which the power supply and ammeter are integrated into circuitry are preferred.

If the applied voltage is too low, the resulting output current is too low (resulting in increased electrical noise); and if the applied voltage is too high, the possibility of electrochemical degradation of the conductive polymer component increases. The amount of voltage used is within a range of between about 5 millivolts and about 300 millivolts, preferably, between about 10 millivolts and about 50 millivolts. The sensitivity of the measurement of the current is within ±2 nanoamperes for a sensor with the size of about 1 centimeter by 1.5 centimeter.

The process of detection is very quick and the sensitivity of the sensor is very high. In fact, as little as 100 parts per billion (ppb) to 500 ppb of analytic pathogen, is readily detectable, and the response is already registered within 5 to 30 seconds from the time of exposure of the sensor to the pathogen 12.

The formulation of the ingredient 7 of the thin film 3 may include a silane selected from a wide range of silanes compatible with different conductive polymers, not just EETMS and 3-APTES which are the preferred silanes. Furthermore, by using different silanes, the degree of electrical conductivity of the conductive polymer component of the ingredient 7 may be varied, giving rise to variations in the sensor response behavior.

The choice of the particular silanes and of the conductive polymer component, as well as their ratios shall be made as a matter of design choice and the criteria for such a design choice is known to those skilled in the art. The alternative silanes and conductive polymers that can be used are described below.

Figure 5:
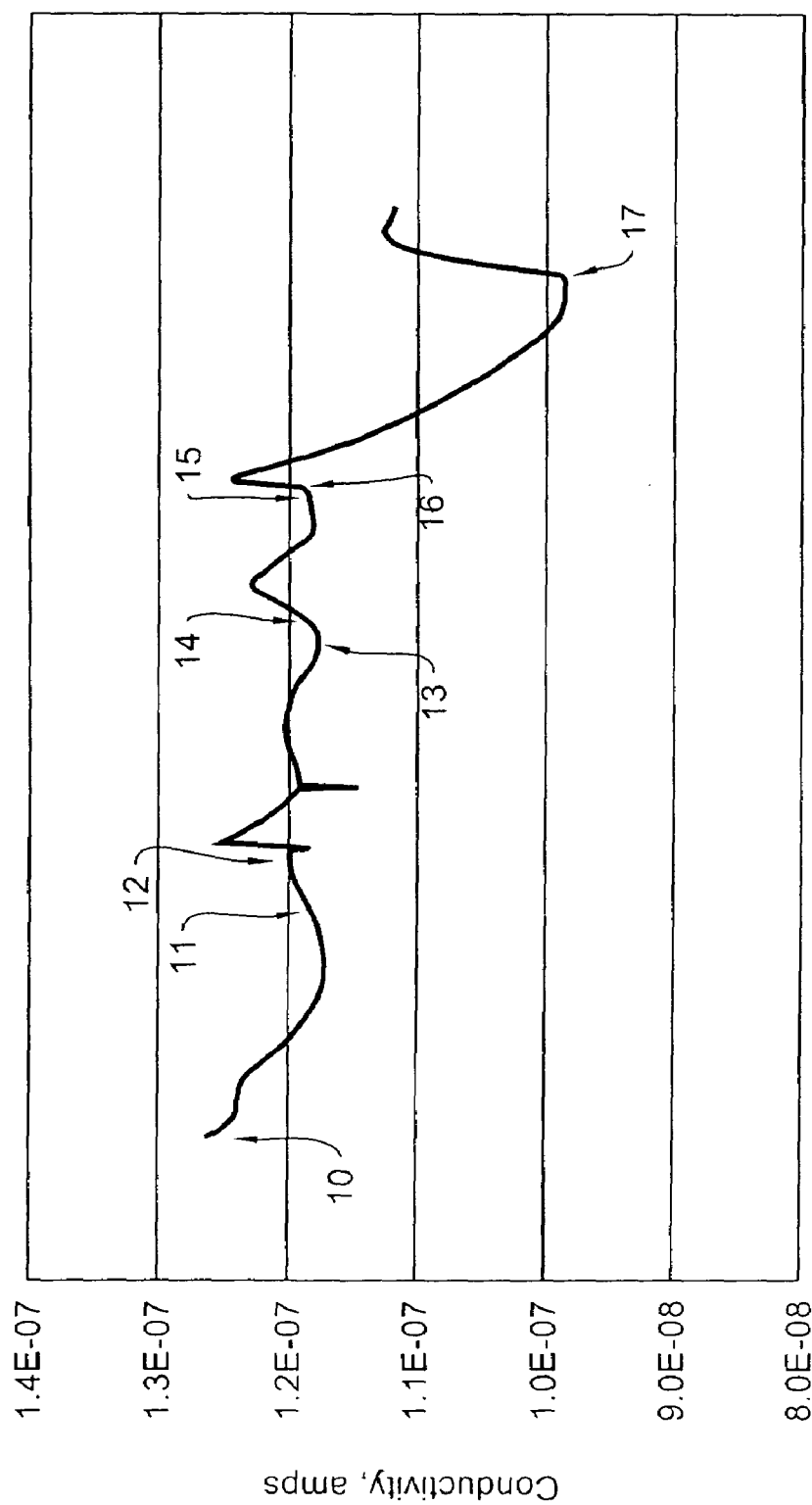
FIGS. 5 and 6 are graphs showing typical responses of the sensor.
Figure 6:
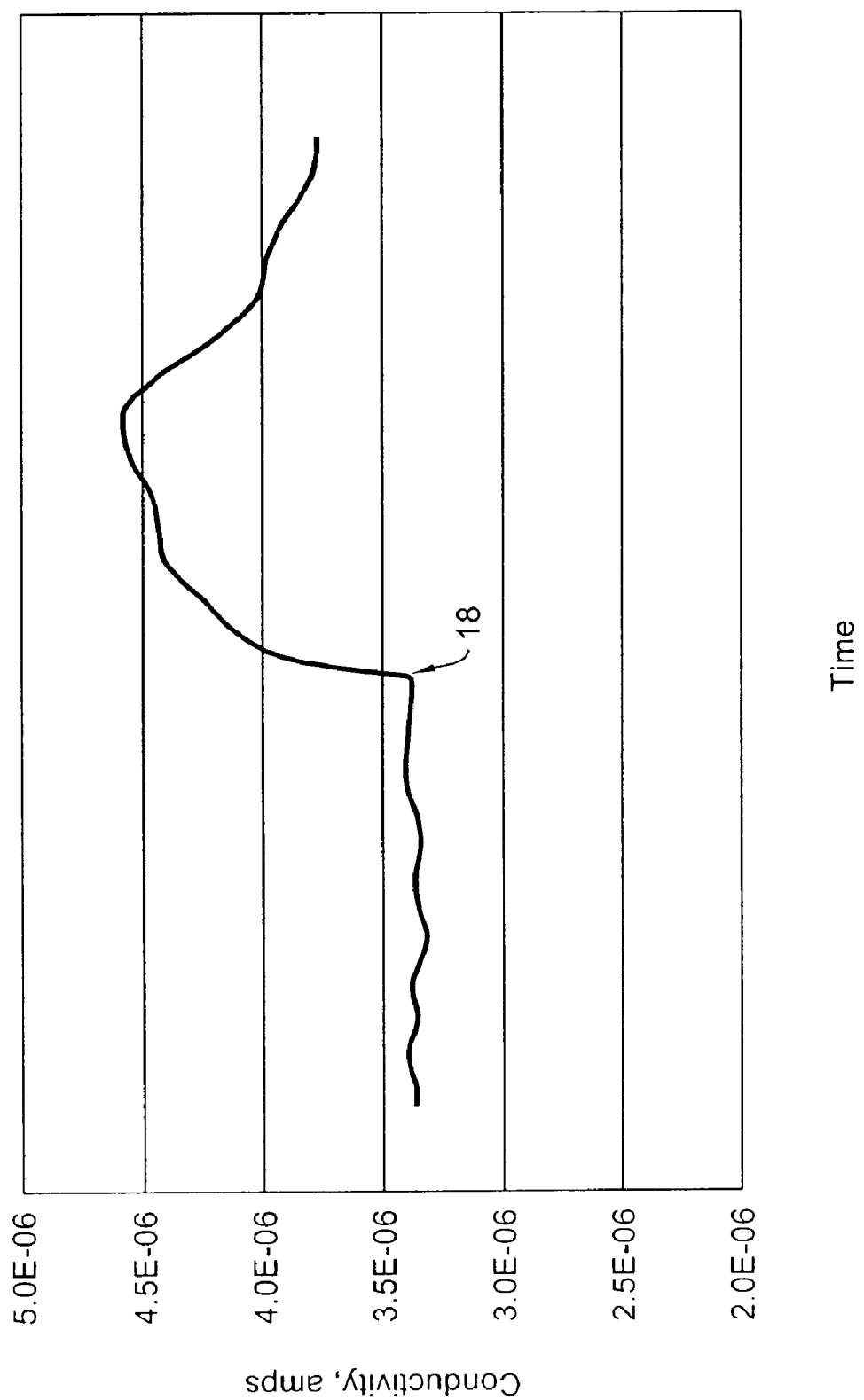

Examples of the results of detection using sensors prepared with ingredients 7 containing different siloxanes are shown in FIGS. 5 and 6. Test samples were prepared and examined as thin films 3 applied to small interdigitated electrodes (IDEs). Response data was obtained using a static enclosed chamber, in which the sample transducer was placed, stabilized and then exposed to a saturated concentration of challenge vapor (about 500 ppb for malathion and about 100 ppb for parathion).

FIGS. 5 and 6 show the conductivity of the ingredient 7 as a function of time when the AChE bioindicator 4 is exposed to malathion and parathion (FIG. 5) or to parathion (FIG. 6). Both malathion and parathion were purchased from Aldrich Chemical Co. of St. Louis, Mo. In both cases PAS was used as a conductive polymer component of the ingredient 7 of film 3, in the amount of about 10% by weight of the siloxane component of the ingredient 7 of film 3.

In case of the malathion/parathion exposure demonstrated in FIGS. 5 and 6, the silane component of the ingredient 7 of the film 3 comprised a blend of EEMTS and 3-APTES taken in a weight ratio of about 1 to 3.5. The ingredient 8 of the film 3 also comprised a blend of EEMTS and 3-APTES taken in a weight ratio of about 1 to 3.5.

In case of the parathion exposure demonstrated in FIG. 6, instead of EEMTS:3-APTES, the ingredient 7 comprised a mixture of tetramethoxysilane (TMOS), Si(OCH$_3$)$_4$, and of 3-glycidoxypropyltrimethoxysilane(GPTMS) shown in (5),

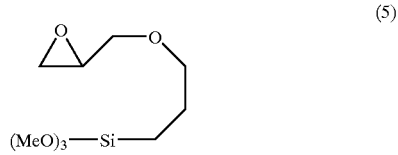

(5)

in a weight ratio of about 1 to 1. The former silane was purchased from Aldrich Chemical Co. of St. Louis, Mo., and the latter from United Chemical Technologies, Inc. of Bristol, Pa. In this case, no siloxane ingredient 8 was used (i.e., open-faced).

FIG. 5 demonstrates the response of the sensor when exposed to malathion, in nitrogen atmosphere. Points 10 and 14 refer to the moments in time when a flow of nitrogen is started and points 11 and 16—when it was stopped. As can be seen, after the exposure to malathion has been initiated (point 12), the current in the circuit 9 briefly shifts upward, then generally decreases, until malathion is removed (point 13). This indicates that the conductivity of the film 3 decreases as a result of either the change in the morphology of film 3 caused by the chemical reaction of AChE with malathion or by the chemical by-products of this reaction, or by some combination of both. If parathion is added instead (point 15), the response on the segment 15–17 is similar to that with malathion, only greater. After parathion is removed (point 17), the conductivity of the film approaches its original value and the sensor baseline is re-established.

FIG. 6 demonstrates a response of another sensor in case of parathion. Here, however, after parathion is added to the environment around the sensor (point 18), an opposite phenomenon is observed for this open-face sensor. The conductivity of film 3 increases due to the same factors as mentioned above in case of malathion, and the current in the circuit 9 increases from about $3.5*10^{-6}$ to about $4.5*10^{-6}$ Amperes.

An overall response from parathion is somewhat stronger, which is attributed to the difference between the by-products generated in reactions (3) and (4) described above. The difference in baseline conductivity indicates a significant difference, possibly due to the degree and nature of doping of these two samples.

Because the malathion and parathion by-products are different, they will modulate polymer conductivity through very different mechanisms. Consequently, a change in polymer electronic structure will not have an equivalent effect for these two pathogens. FIGS. 5 and 6 clearly demonstrate that as anticipated, the response behavior of the conductive polymer component of the ingredient 7 is by-product specific and furthermore, may be significantly altered by modification of the electronic state of the polymer. Alternatively, the different by-products may result in different degrees of molar volume changes which could account for the observed conductivity modulation. Regardless, the different response to similar analytes may then be used as the basis for building transducer arrays. Therefore with this invention, the speciation of pathogenic analytes may be accomplished based on discrimination of the byproducts of the enzyme-substrate interaction.

An ingredient 8 of the sandwich film 3 contains no conductive polymer, but serves to further stabilize the bioindicator 4. The formulation of this layer is important in that it must be well adhered and crack-free and provide good porosity for rapid permeation of the target pathogen(s). However, because of the permeability of the ingredient 7, the components for the ingredient 8 should not change the state of doping of the conductive polymer incorporated in the ingredient 7. As mentioned above, the ingredient 8 is used in the preferred embodiment, but alternatively it does not have to be used and the sensor will remain viable even without the ingredient 8.

Figure 4B:
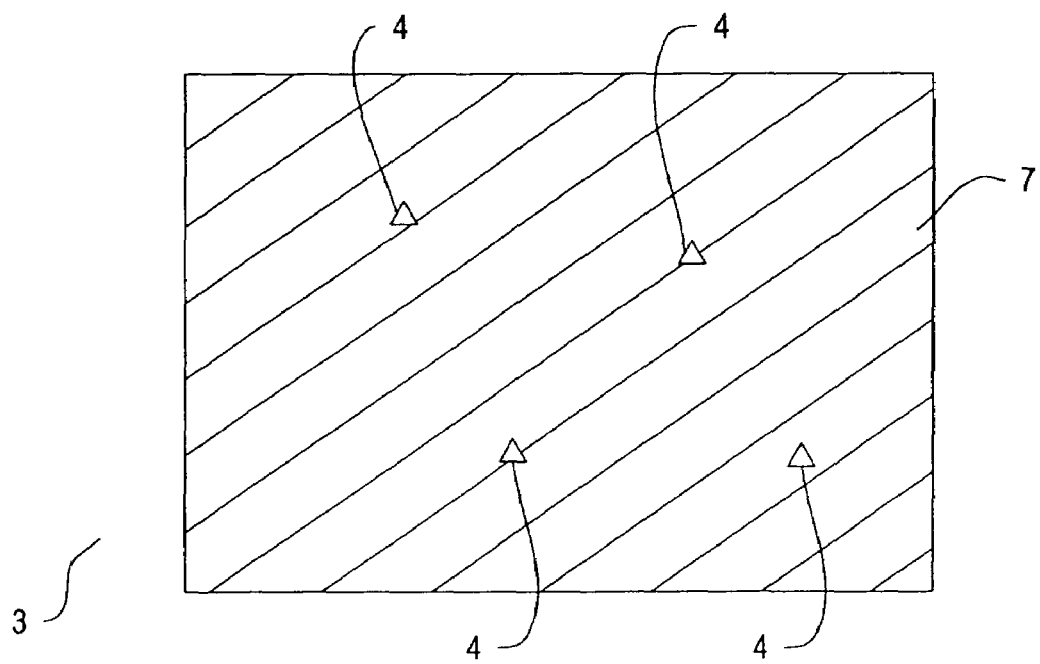
FIG. 4b is a schematic diagram showing the internal structure of a portion of an alternative embodiment of the sensor in more detail.

If both ingredients 7 and 8 are used, they form a complex tridimensional interpenetrating polymeric network, and the AChE bioindicator is ensconced within this network. In the alternative case, when only the ingredient 7 is used, the AChE bioindicator 4 is directly embedded in the film 3, as shown on FIG. 4b, the film 3 in this embodiment comprising only the ingredient 7.

Therefore, the choice of the ingredient 8, if used, must be coordinated with the requirements of the ingredient 7. Either the same silane should be used in both ingredients 7 and 8 or the ingredient 8 comprises silanes with limited functionality which may not activate or deactivate the conductive polymer.

Described herein is a sensor and method for detecting biological and chemical agents comprising metal interdigitized electrodes coated with hybrid polymer-based conducting film and an instrument for applying electrical voltage to the electrodes and registering the change in electrical current. The hybrid film also comprises indicator biomolecules encapsulated-within the film or attached to it. The bioindicator molecules preferably comprise enzyme acetylcholinesterase. When these indicator biomolecules come in a contact with a pathogen, chemical and/or morphological changes occur in the film and electrical current flowing through the electrodes is modulated. The pathogen comprises inhibitors of enzymes, preferably organophosphates, thiophosphates or phosphonates. The change in current indicates the presence of a biological and chemical agent and is registered.

In this application (including in the description, claims, drawings, and abstract), the phrases "bioindicator molecule," "bioindicator," "bioindicator material," and "indicator biomolecule" are synonymous (i.e., equivalent to each other).

Having described the invention in connection with several embodiments thereof, modification will now suggest itself to those skilled in the art. As such, the invention is not to be limited to the described embodiments except as required by the appended claims.

All of the numerical and quantitative measurements set forth in this application (including in the examples and in the claims) are approximations.

The invention illustratively disclosed or claimed herein suitably may be practiced in the absence of any element which is not specifically disclosed or claimed herein. Thus, the invention may comprise, consist of, or consist essentially of the elements disclosed or claimed herein.

The following claims are entitled to the broadest possible scope consistent with this application. The claims shall not necessarily be limited to the preferred embodiments or to the embodiments shown in the examples.

We claim:

1. A sensor for detecting a chemical or biological molecule or a pathogen, said sensor comprising:
   a dielectric substrate;
   a plurality of interdigitated electrodes attached to said substrate;
   a film applied over said plurality of interdigitated electrodes;

a film applied over said plurality of interdigitated electrodes, wherein said film comprises a conductive polymer and a first and a second sol-gel derived material;

one or more bioindicator molecules incorporated within said film, wherein said bioindicator molecule is ensconced within an interpenetrating network, wherein said network is formed by said first sol-gel derived material and said second sol-gel derived material; and an instrument to measure an electric current flowing through said plurality of interdigitated electrodes.

2. The sensor of claim 1, wherein said dielectric substrate is fabricated of a material selected from the group consisting of quartz, glass, ceramic, and plastic.

3. The sensor of claim 1, wherein each of said plurality of interdigitated electrodes has a generally rectangular shape in a cross-section.

4. The sensor of claim 1, wherein each of said plurality of interdigitated electrodes has a width within a range of between about 5 micrometers and about 25 micrometers.

5. The sensor of claim 4, wherein said width is about 15 micrometers.

6. The sensor of claim 1, wherein said plurality of interdigitated electrodes includes at least one pair of electrodes defining a gap, wherein the gap is within a range of between about 5 micrometers and about 25 micrometers.

7. The sensor of claim 6, wherein said gap is about 15 micrometers.

8. The sensor of claim 1, wherein said bioindicator molecule is selected from the group consisting of enzymes, antibodies, and antibiotics.

9. The sensor of claim 8, wherein said enzymes are selected from the group consisting of acetylcholinesterase, glucose oxidase, α-amylase, glutamate dehydrogenase, and organophosphorous hydrolase.

10. The sensor of claim 8, wherein said antibodies are selected from the group consisting of *escherichia coli* serotype 157:H7 IgG, goat anti-human IgG(γ), goat anti-*bacillus anthracis antisera* and anti-TNT IgG.

11. The sensor of claim 8, wherein said antibiotics are selected from the group consisting of penicillin, naficillin, and oxacillin.

12. The sensor of claim 1, wherein said instrument to measure said electric current is comprised of a voltage source and an ammeter.

13. The sensor of claim 1, wherein said plurality of interdigitated electrodes are fabricated of gold.

14. The sensor of claim 1, wherein said chemical or biological molecule is selected from the group consisting of inhibitors of enzymes, antigens of antibodies, and reactants of antibiotics.

15. The sensor of claim 14, wherein said inhibitors are selected from the group consisting of organophosphates, organothiophosphates, organophosphonates, and mixtures thereof.

16. The sensor of claim 1, wherein said plurality of interdigitated electrodes are attached to said substrate by an adhesion layer.

17. The sensor of claim 16, wherein said adhesion layer comprises a material selected from the group consisting of titanium and an alloy of titanium and tungsten.

18. The sensor of claim 1, wherein said conductive polymer is selected from the group consisting of polyaniline, polythiophene, polypyrrole, and derivatives thereof.

19. The sensor of claim 1, wherein said indicator biomolecule is ensconced within said first sol-gel derived material.

20. The sensor of claim 1, wherein said first and second sol-gel derived materials each comprise a product of gelation of two or more organosilicon compounds.

21. The sensor of claim 20, wherein said organosilicon compounds are selected from the group consisting of monofunctional silanes, difunctional silanes, trifunctional silanes, tetrafunctional silanes, derivatized silanes, and mixtures thereof.

22. The sensor of claim 21, wherein said monofunctional silanes are selected from the group consisting of octadecyldimethylmethoxysilane, other monofunctional silanes, and mixtures thereof; wherein the other monofunctional silanes are hydrolyzable to form silanols that can dehydrate to form sol-gels.

23. The sensor of claim 21, wherein said difunctional silanes are selected from the group consisting of methyldimethoxysilane, dimethyldiethoxysilane, other difunctional silanes, and mixtures thereof; wherein the other difunctional silanes are hydrolyzable to form silanols that can dehydrate to form sol-gels.

24. The sensor of claim 21, wherein said trifunctional and tetrafunctional silanes are selected from the group consisting of methyltrimethoxysilane, octadecyltrichlorosilane, octadecyltriethoxysilane, tetramethoxysilane, phenyltrimethoxysilane, 1,4-bis(trimethoxysilylethyl)benzene, other trifunctional and tetrafunctional silanes, and mixtures thereof; wherein the other trifunctional and tetrafunctional silanes are hydrolyzable to form silanols that can dehydrate to form sol-gels.

25. The sensor of claim 21, wherein said derivatized silanes are selected from the group consisting of 2-(3,4-epoxycyclohexyl)ethyltrimethoxysilane, 3-aminopropyltrimethoxysilane, 3-aminopropyltriethoxysilane, 3 glycidoxypropyltrimethoxysilane, 4-aminobutyldimethylmethoxysilane, N-(2 aminoethyl)-3-aminopropylmethyldimethoxysilane, 5 (bicycloheptenyl)triethoxysilane, dicyclohexyldimethoxysilane, 3 glycidylpropyltrimethoxysilane, other derivatized silanes, and mixtures thereof; wherein the other derivatized silanes are hydrolyzable to form silanols which can dehydrate to form sol-gels.

26. A method for detecting a chemical or biological molecule or a pathogen, the method comprising:
(a) exposing the sensor claimed in claim 1 to the chemical or biological molecule or pathogen;
(b) applying an electric voltage to the plurality of interdigitated electrodes of the sensor;
(c) measuring a change in an electric current flowing through the plurality of interdigitated electrodes.

27. The sensor of claim 1, wherein said bioindicator molecule is deoxyhemoglobin.

28. A method for detecting a chemical or biological molecule or a pathogen, the method comprising the steps of:

disposing a plurality of interdigitated electrodes on a dielectric substrate;

applying a film over said plurality of interdigitated electrodes, wherein said film comprises a conductive polymer and a first and second sol-gel derived material;

incorporating one or more bioindicator molecules into said film by embedding said bioindicator molecule within said film or attaching said bioindicator molecule to said film, wherein said bioindicator molecule is ensconced within an interpenetrating network, wherein said network is formed by said first sol-gel derived material and said second sol-gel derived material;

exposing said film to an environment containing said chemical or biological molecule or pathogen;

applying an electric voltage to said plurality of interdigitated electrodes; and measuring a change in an electric current flowing through said plurality of interdigitated electrodes, said change being caused by interaction of said chemical or biological molecule or pathogen with said film.

29. The method of claim 28, wherein said dielectric substrate is fabricated of a material selected from the group consisting of quartz, glass, ceramic, and plastic.

30. The method of claim 28, wherein each of said plurality of interdigitated electrodes is attached to said substrate with use of an adhesion layer.

31. The method of claim 30, wherein said adhesion layer comprises a material selected from the group consisting of titanium and an alloy of titanium and tungsten.

32. The method of claim 28, wherein each of said plurality of interdigitated electrodes has a generally rectangular shape in a cross-section.

33. The method of claim 28, wherein each of said plurality of interdigitated electrodes has a width within a range of between about 5 micrometers and about 25 micrometers.

34. The method of claim 33, wherein said width is about 15 micrometers.

35. The method of claim 28, wherein said plurality of interdigitated electrodes includes at least one pair of electrodes defining a gap, wherein the gap is within a range of between about 5 micrometers and about 25 micrometers.

36. The method of claim 35, wherein said gap is about 15 micrometers.

37. The method of claim 28, wherein said bioindicator molecule is selected from the group consisting of enzymes, antibodies, and antibiotics.

38. The method of claim 37, wherein said enzymes further comprise acetylcholinesterase.

39. The method of claim 37, wherein said enzymes are selected from the group consisting of glucose oxidase, α-amylase, glutamate dehydrogenase, and organophosphorous hydrolase.

40. The method of claim 37, wherein said antibodies are selected from the group consisting of *escherichia coli* serotype 157:H7 IgG, goat anti-human IgG(γ), goat anti-*bacillus anthracis antisera* and anti-TNT IgG.

41. The method of claim 28, wherein an amount of said voltage is between about 5 millivolts and about 300 millivolts.

42. The method of claim 41, wherein said amount of said voltage is between about 10 millivolts and about 50 millivolts.

43. The method of claim 28, wherein said plurality of interdigitated electrodes are fabricated of an electrically conductive material comprising gold.

44. The method of claim 28, wherein said chemical or biological molecule is selected from the group consisting of inhibitors of enzymes, antigens of antibodies, and reactants of antibodies.

45. The method of claim 44, wherein said antibiotics are selected from the group consisting of penicillin, naficillin, and oxacillin.

46. The method of claim 44, wherein said inhibitors are selected from the group consisting of organophosphates, organothiophosphates, organophosphonates, and mixtures thereof.

47. The method of claim 28, wherein said bioindicator molecule is ensconced within said first sol-gel derived material.

48. The method of claim 28, wherein said first and second sol-gel derived materials each comprise a product of gelation of two or more organosilicon compounds.

49. The method of claim 48, wherein said organosilicon compounds are selected from the group consisting of monofunctional silanes, difunctional silanes, trifunctional silanes, tetrafunctional silanes, derivatized silanes, and mixtures thereof.

50. The method of claim 49, wherein said monofunctional silanes are selected from the group consisting of octadecyldimethylmethoxysilane, other monofunctional silanes, and mixtures thereof; wherein the other monofunctional silanes are hydrolyzable to form silanols that can dehydrate to form sol-gels.

51. The method of claim 49, wherein said difunctional silanes are selected from the group consisting of methyldimethoxysilane, dimethyldiethoxysilane, other difunctional silanes, and a mixture thereof; wherein the other difunctional silanes are hydrolyzable to form silanols that can dehydrate to form sol-gels.

52. The method of claim 49, wherein said trifunctional and tetrafunctional silanes are selected from the group consisting of methyltrimethoxysilane, octadecyltrichlorosilane, octadecyltriethoxysilane, tetramethoxysilane, phenyltrimethoxysilane, 1,4-bis(trimethoxysilylethyl)benzene, other trifunctional and tetrafunctional silanes, and mixtures thereof; wherein the other trifunctional and tetrafunctional silanes are hydrolyzable to form silanols that can dehydrate to form sol-gels.

53. The method of claim 49, wherein said derivatized silanes are selected from the group consisting of 2-(3,4-epoxycyclohexyl)ethyltrimethoxysilane, 3-aminopropyltrimethoxysilane, 3-aminopropyltriethoxysilane, 3-glycidoxypropyltrimethoxysilane, 4-aminobutyldimethylmethoxysilane, N-(2-aminoethyl)-3-aminopropylmethyldimethoxysilane, 5-(bicycloheptenyl)triethoxysilane, dicyclohexyldimethoxysilane, 3-glycidylpropyltrimethoxysilane, other derivatized silanes, and mixtures thereof wherein the other derivatized silanes are hydrolyzable to form silanols which can dehydrate to form sol-gels.

54. The sensor as claimed in claim 1, wherein the conductive polymer comprises polyaniline, polythiophene, and/or polypyrrole; wherein the polyaniline, the polythiophene, and the polypyrrole are each optionally doped with one or more counterions; and wherein the polyaniline, the polythiophene, and the polypyrrole each optionally include a ring having a methoxy substituent, an ethoxy substituent, a trifluoromethyl substituent, and/or an amino substituent.

55. The sensor as claimed in claim 54, wherein the counterions are selected from the group consisting of chloride, bisulfate, sulfonic acid, and dodecylbenzene sulfonic acid.

56. The sensor as claimed in claim 1, wherein the first sol-gel derived material forms a first sol-gel layer, wherein the second sol-gel derived material forms a second sol-gel layer on top of and in contact with the first sol-gel layer, and wherein the bioindicator molecule is sandwiched between the first sol-gel layer and the second sol-gel layer.

57. The sensor as claimed in claim 1, wherein the first sol-gel derived material forms a first sol-gel layer, wherein the second sol-gel derived material forms a second sol-gel layer on top of and in contact with the first sol-gel layer, and wherein the bioindicator molecule is ensconced or encapsulated within either the first sol-gel layer or the second-sol gel layer.

58. The sensor as claimed in claim 57, wherein the first sol-gel layer is in electrical contact with the interdigitated electrodes, and wherein the polymer is incorporated into the first sol-gel layer.

59. The sensor as claimed in claim 57, wherein the second sol gel layer is in electrical contact with the interdigitated electrodes, and wherein the polymer is incorporated into the second sol-gel layer.

60. The method as claimed in claim 28, wherein the first sol-gel derived material forms a first sol-gel layer, wherein the second sol-gel derived material forms a second sol-gel layer on top of and in contact with the first sol-gel layer, and wherein the bioindicator molecule is sandwiched between the first sol-gel layer and the second sol-gel layer.

61. The method as claimed in claim 28, wherein the first sol-gel derived material forms a first sol-gel layer, wherein the second sol-gel derived material forms a second sol-gel layer on top of and in contact with the first sol-gel layer, and wherein the bioindicator molecule is ensconced or encapsulated within either the first sol-gel layer or the second-sol gel layer.

62. The method as claimed in claim 61, wherein the first sol-gel layer is in electrical contact with the interdigitated electrodes, and wherein the polymer is incorporated into the first sol-gel layer.

63. The method as claimed in claim 61, wherein the second sol-gel layer is in electrical contact with the interdigitated electrodes, and wherein the polymer is incorporated into the second sol-gel layer.

64. The method as claimed in claim 28, wherein the chemical or biological molecule or pathogen is in a fluid.

65. The method as claimed in claim 28, wherein the chemical or biological molecule or pathogen is in a gas or a liquid.

66. The method as claimed in claim 28, wherein the chemical or biological molecule or pathogen is in air or an aqueous environment.

67. The method of claim 28, wherein said bioindicator molecule is deoxyhemoglobin.

* * * * *